US009164477B2

(12) United States Patent
Verheijen

(10) Patent No.: US 9,164,477 B2
(45) Date of Patent: Oct. 20, 2015

(54) CURRENT LEAKAGE CORRECTION IN HUMID ENVIRONMENTS

(71) Applicant: XEROX CORPORATION, Norwalk, CT (US)

(72) Inventor: Hendrikus Adrianus Anthonius Verheijen, Venray (NL)

(73) Assignee: Xerox Corporation, Norwalk, CT (US)

( * ) Notice: Subject to any disclaimer, the term of this patent is extended or adjusted under 35 U.S.C. 154(b) by 8 days.

(21) Appl. No.: 14/093,582

(22) Filed: Dec. 2, 2013

(65) Prior Publication Data

US 2015/0153709 A1  Jun. 4, 2015

(51) Int. Cl.
| G03G 15/00 | (2006.01) |
| G03G 21/20 | (2006.01) |
| G01N 27/00 | (2006.01) |
| G03G 15/16 | (2006.01) |

(52) U.S. Cl.
CPC .............. *G03G 21/203* (2013.01); *G01N 27/00* (2013.01); *G03G 15/1675* (2013.01); *G03G 15/80* (2013.01)

(58) Field of Classification Search
CPC ................ G03G 2215/00776; G03G 15/5029; G03G 15/5041; G03G 15/2053; G03G 15/5058; G03G 15/5062; G03G 15/55; G03G 2215/00042; G03G 15/0131; G03G 15/1675; G03G 15/20; G03G 15/2039; G03G 15/2096
See application file for complete search history.

(56) References Cited

U.S. PATENT DOCUMENTS

| 5,200,589 | A | 4/1993 | Kim |
| 5,715,131 | A * | 2/1998 | Matsuyama et al. .......... 361/225 |
| 5,757,195 | A | 5/1998 | Bird |
| 5,837,884 | A | 11/1998 | Kimura et al. |
| 6,079,121 | A * | 6/2000 | Khadkikar et al. ............. 34/528 |
| 6,670,557 | B2 | 12/2003 | Gehrke et al. |
| 6,953,921 | B2 | 10/2005 | Kim |
| 7,053,347 | B1 | 5/2006 | Lee et al. |
| 7,999,416 | B2 | 8/2011 | Lalonge |
| 2002/0136664 | A1 * | 9/2002 | Lee et al. ........................ 422/98 |

FOREIGN PATENT DOCUMENTS

EP  1 011 199  3/2003

* cited by examiner

*Primary Examiner* — Roy Y Yi
(74) *Attorney, Agent, or Firm* — Gibb & Riley, LLC

(57) ABSTRACT

Apparatuses include a voltage divider that is connected to a current source, a humidity sensor within an internal humid location of an apparatus, and an amplifier connected to the voltage divider and the humidity sensor. The humidity sensor produces a current signal that increases with increases in the humidity level and the amplifier amplifies the signal produced by the humidity sensor to produce compensating output current. The amplifier provides amplification of the signal produced by the humidity sensor at a level that increases with increases of the primary output current. Thus, the amplifier provides the amplification of the signal produced by the humidity sensor at a level to make the compensating output current equal to the leakage current. This causes the electrical load element to receive the primary output current combined with the compensating output current as a power supply current that is unaffected by the leakage current.

20 Claims, 5 Drawing Sheets

CURRENT LEAKAGE CORRECTION IN HUMID ENVIRONMENTS

BACKGROUND

Systems and methods herein generally relate to current leakage in circuitry and to correcting for current leakage in circuits that are used in humid environments.

For some high-voltage power supply applications, current leakage from the high-voltage output circuit should be limited because the amount of current leakage correspondingly reduces the amount of output current. One example of such an application is a high-voltage DC current source for charging a bias transfer roll (BTR) in an electrostatic printer. Typically, voltages of up to 6 kV are required in a bias transfer roll to obtain currents well below 100 uA. The current source in a bias transfer roll must also have an accuracy of uA's, so any current leakage can substantially decrease the performance of the bias transfer roll.

High-voltage circuits on printed circuit boards (PCB's) can easily leak current if they are situated in a humid environment. The PCB material has the ability to absorb water, which makes the surface relatively conductive, resulting in current leakage. Factors that contribute to current leakage are the material properties and the level of contamination of the surface (flux residue) of the PCB. Further, this effect is especially noticeable at high voltages and low currents, where operation relies on the insulating properties.

There are a number of methods used to prevent or reduce such current leakage. One method is to encapsulate the high-voltage circuit in a housing so that it is not exposed to the humid environment. These (potting) techniques are very effective, but relatively costly. If the high-voltage output must be available on the PCB for interfacing, this technique is not adequate.

Another method is to use shielding techniques, where the high-voltage (circuits) are surrounded or separated by conductive shields. The leakage current, picked-up by the shield, is measured and used for correcting the output current or voltage accordingly. This works best if the shield is nearby the high-voltage circuit and completely surrounds it. However, such shields increase the leakage and can potentially cause insulation breakdown (arcing/tracking). Also, on single-sided PCB's the leakage across the top side surface (where there is no shield) cannot be measured.

Another method, commonly used in printing machines, is to utilize a humidity sensor. With this, the relative humidity of the general machine environment is monitored and fed back to the processor unit for changing the setpoints required for maintaining the image quality. One of these setpoints is the BTR current. This approach does not take into account that the (relative) humidity in the area where the high-voltage power supply (HVPS) resides can be completely different. Also, the contamination degree of the HVPS PCB surface and the content of previously absorbed water in the PCB is not a constant factor over time. Furthermore, such methods rely on an HVPS manufactured with controlled PCB cleanliness.

SUMMARY

Exemplary apparatuses herein have an internal humid location (e.g., an internal location that experiences a humidity level that is higher relative to the humidity levels of areas external to the apparatus). These apparatuses utilize at least one current source within the internal humid location of the apparatus, and this current source can experience leakage current that increases with increases in the humidity level. Also, an electrical load element is connected to the current source. The current source provides primary output current to the electrical load element. However, increases in the leakage current caused by the increased humidity correspondingly decrease the primary output current provided to the electrical load element.

In order to address such issues, the apparatuses herein include an optional voltage divider that is connected to the current source, a humidity sensor within the internal humid location of the apparatus, and an amplifier connected to the voltage divider and the humidity sensor. The humidity sensor produces a current signal that increases with increases in the humidity level and the amplifier amplifies the signal produced by the humidity sensor to produce compensating output current. The amplifier provides amplification of the signal produced by the humidity sensor at a level that increases with increases of the primary output current, because the primary output current is provided to the amplifier by the voltage divider (if included). Thus, the amplifier provides the amplification of the signal produced by the humidity sensor at a level to make the compensating output current equal to the leakage current.

Further, the amplifier provides the compensating output current to the electrical load element with the primary output current. This causes the electrical load element to receive the primary output current combined with the compensating output current as a power supply current that is unaffected by the leakage current.

In one example, the humidity sensor can include opposing terminals, interleaved conductors connected to the terminals, and electrical insulation between the interleaved conductors. Further, the current source and the humidity sensor can be located on the same printed circuit board and can have substantially similarly sized and spaced elements (e.g., substantially similarly sized conductors and insulators) that react substantially similarly to the contamination and humidity that is found within the humid location of the apparatus. This allows the amplified signal from the humidity sensor to match the leakage current experienced by the current source, and thereby serve as a highly effective compensating output current supplementing the primary output current to allow the electrical load to receive a power supply current that is unaffected by the leakage current.

Exemplary printing apparatuses herein have a printing engine and an internal humid location within said printing engine (e.g., an internal location that experiences a humidity level that is higher relative to the humidity levels of areas external to the printing engine). These printing apparatuses utilize at least one current source within the internal humid location of the printing apparatus, and this current source can experience leakage current that increases with increases in the humidity level. Also, an electrical load element is connected to the current source. The current source provides primary output current to the electrical load element. However, increases in the leakage current caused by the increased humidity correspondingly decrease the primary output current provided to the electrical load element.

In order to address such issues, the printing apparatuses herein include an optional voltage divider that is connected to the current source, a humidity sensor within the internal humid location of the printing apparatus, and an amplifier connected to the voltage divider and the humidity sensor. The humidity sensor produces a current signal that increases with increases in the humidity level and the amplifier amplifies the signal produced by the humidity sensor to produce compensating output current. The amplifier provides amplification of the signal produced by the humidity sensor at a level that increases with increases of the primary output current, because the primary output current is provided to the amplifier by the voltage divider (if included). Thus, the amplifier provides the amplification of the signal produced by the humidity sensor at a level to make the compensating output current equal to the leakage current.

Further, the amplifier provides the compensating output current to the electrical load element with the primary output current. This causes the electrical load element to receive the primary output current combined with the compensating output current as a power supply current that is unaffected by the leakage current.

In one example, the humidity sensor can include opposing terminals, interleaved conductors connected to the terminals, and electrical insulation between the interleaved conductors. Further, the current source and the humidity sensor can be located on the same printed circuit board and can have substantially similarly sized and spaced elements (e.g., substantially similarly sized conductors and insulators) that react substantially similarly to the contamination and humidity that is found within the humid location of the printing apparatus. This allows the amplified signal from the humidity sensor to match the leakage current experienced by the current source, and thereby serve as a highly effective compensating output current supplementing the primary output current to allow the electrical load to receive a power supply current that is unaffected by the leakage current.

These and other features are described in, or are apparent from, the following detailed description.

BRIEF DESCRIPTION OF THE DRAWINGS

Various exemplary systems and methods are described in detail below, with reference to the attached drawing figures, in which.

DETAILED DESCRIPTION

As mentioned above there are a number of methods used to prevent or reduce such current leakage; however, each suffers from numerous issues. Therefore, exemplary apparatuses herein provide a humidity-sensitive element in the PCB layout. For example, the humidity-sensitive element (humidity sensor) can be a small area with a comb pattern of conductors and insulators and two terminals connected to each of the interleaved tracks.

The humidity sensor is connected to a high-impedance transresistance amplifier where a voltage is applied that is proportional to the output voltage of the high-voltage current source. The transresistance amplifier converts the sensor current to a voltage that represents the current leakage at the high-voltage output. The voltage is used for correcting the HVPS output current and is a measure of the local humidity in conjunction with the PCB's water absorption and adsorption. The high-voltage circuit and sensor are exposed to the same humidity because they both are located on the same PCB material with the same surface condition. Therefore, because the appropriate scaling is used in the conversion circuit, the correction voltage effectively compensates for the output current leakage caused by high humidity.

Figure 1:
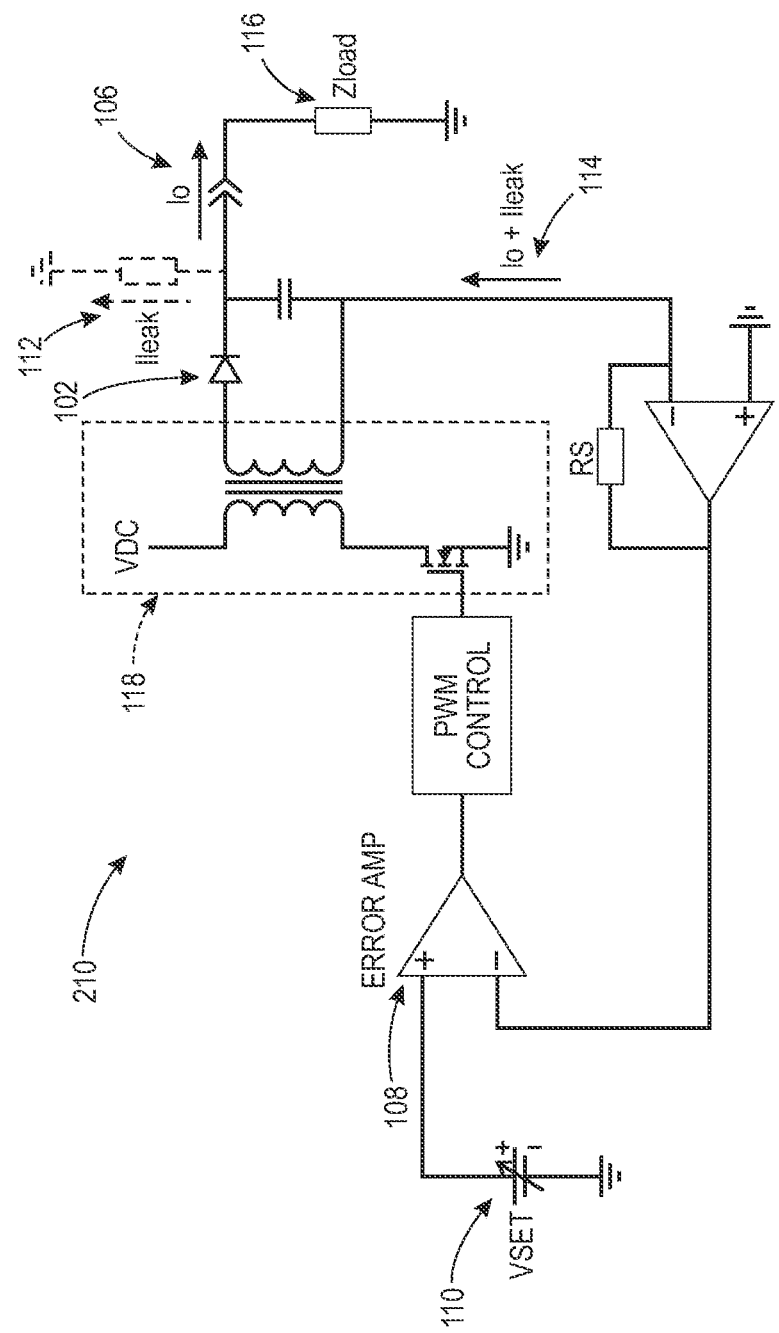
FIG. 1 is a schematic diagram illustrating devices herein.

FIG. 1 shows a schematic representation of a typical high-voltage current source. In FIG. 1, a flyback converter 118 with rectification 102 is used for generating the DC high-voltage. In FIG. 1, Io is the output current 106 and is supplied to a load 116. When there is no leakage (Ileak=0), the voltage at the inverting input of the error amplifier 108 is Io·Rs. The output current 106 can be set (by the voltage source 110) with VSET according Io=VSET/Rs. If there is leakage 112, the voltage at the inverting input of the error amplifier 108 is (Io+Ileak)·Rs and consequently the output current 106 Io=VSET/Rs−Ileak. In words, the output current 106 is Ileak lower than expected because the leakage current 112 is considered to be a component of the output current (as shown by item 114) and, therefore, while this circuit is somewhat effective, the error amplifier 108 may not properly compensate for the leakage 112.

Figure 2:
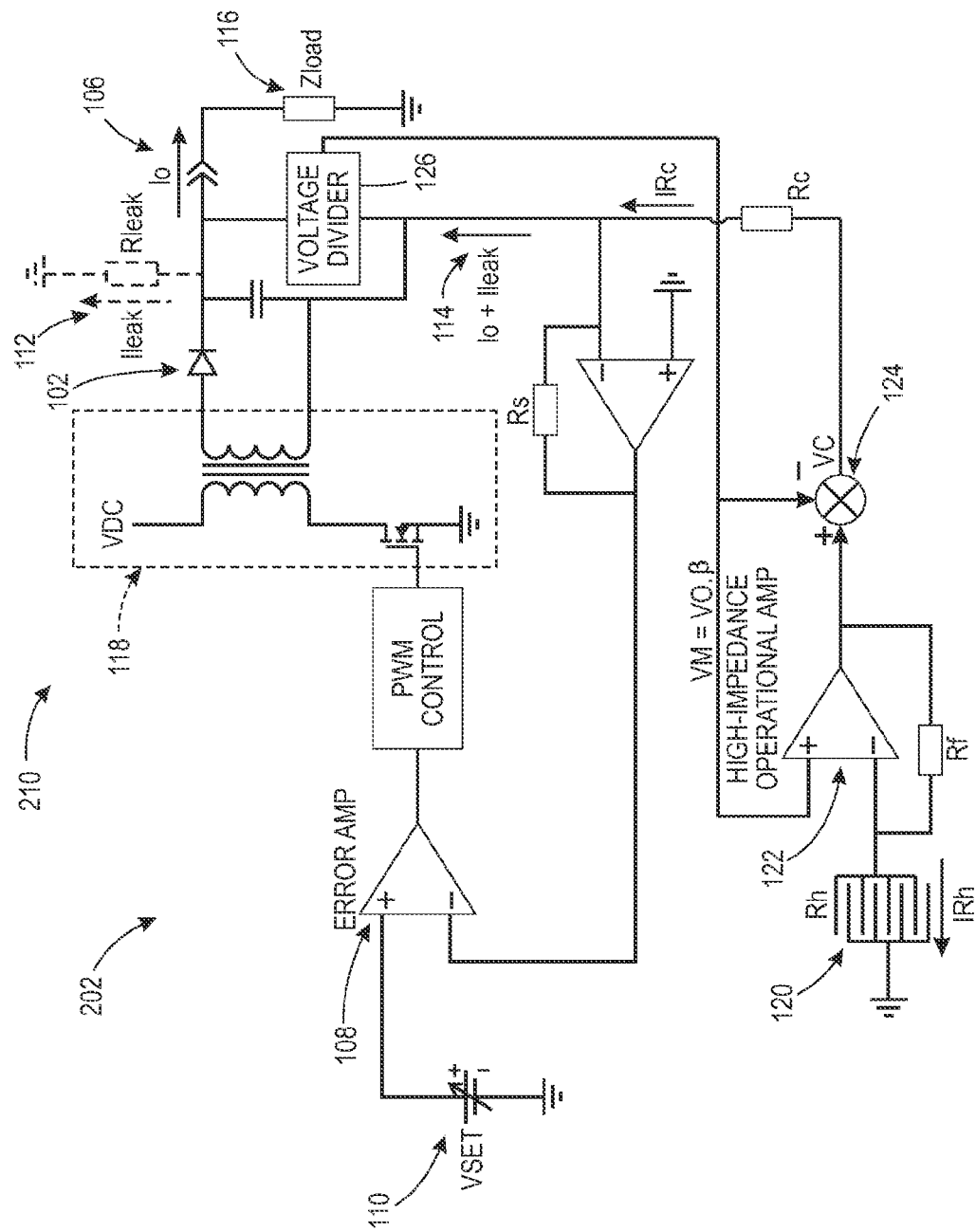
FIG. 2 is a schematic diagram illustrating devices herein.

In the drawings herein, the same identification numbers represent the same or similar components. In FIG. 2, a humidity sensor 120 with transresistance amplifier 122, a subtraction logic element 124, and a voltage divider 126 are included to address such issues. In FIG. 2, Rh represents the resistivity of the humidity sensor 120 and the leakage 112 can be modeled with a resistor Rleak.

In the system shown in FIG. 2, current IRc compensates for Ileak 112, to allow the inverting input of the error amplifier 108 to receive Io·Rs as if there was no leakage.

The output of the transresistance amplifier 122 equals:

$$VA = VM + IRh \cdot Rf$$

And:

$$VC = VA - VM = IRh \cdot Rf$$

So the compensation current IRc equals:

$$IRc = \frac{VC}{Rc} = IRh \cdot \frac{Rf}{Rc}$$

This is equal to Ileak 112:

$$IRh \cdot \frac{Rf}{Rc} = Ileak \quad (1)$$

The foregoing shows that the current through the humidity sensor 120 (IRh) is proportional to the leakage current 112. This is valid for all humidity levels, but also for all output voltage levels (VO). More specifically, since the leakage current 112 depends on the output voltage VO from current source 210 as sensed by the voltage divider 126, the same dependency is required for IRh by transmission of VM=VO·β from the voltage divider 126 through the transresistance amplifier 122. More specifically, the voltage divider 126 is used for:

$$IRh = \frac{VM}{Rh} = \frac{VO \cdot \beta}{Rh}$$

Substitution in (1):

$$\frac{VO \cdot \beta \cdot Rf}{Rh \cdot Rc} = Ileak$$

Or:

$$\frac{VO \cdot \beta \cdot Rf}{Rh \cdot Rc} = \frac{VO}{Rleak}$$

VO can be eliminated:

$$\frac{\beta \cdot Rf}{Rh \cdot Rc} = \frac{1}{Rleak}$$

Writing this differently, results in:

$$Rh = \frac{Rf}{Rc \cdot \beta} \cdot Rleak \qquad (2)$$

Those ordinarily skilled in the art would understand that the various resistive elements (Rf, Rc, β, etc.) can be adjusted and customized to perform the correct scaling for each individual specific situation, as required. Further, those ordinarily skilled in the art would understand that FIGS. 1 and 2 are merely two specific examples and that the claims presented below are applicable to more generalized structures (both analog and digital) such as the generalized structure shown in FIGS. 3-5. Thus, FIG. 2 is just a representation of the operations required. There are more implementation possibilities, both analog and digitally.

Figure 3:
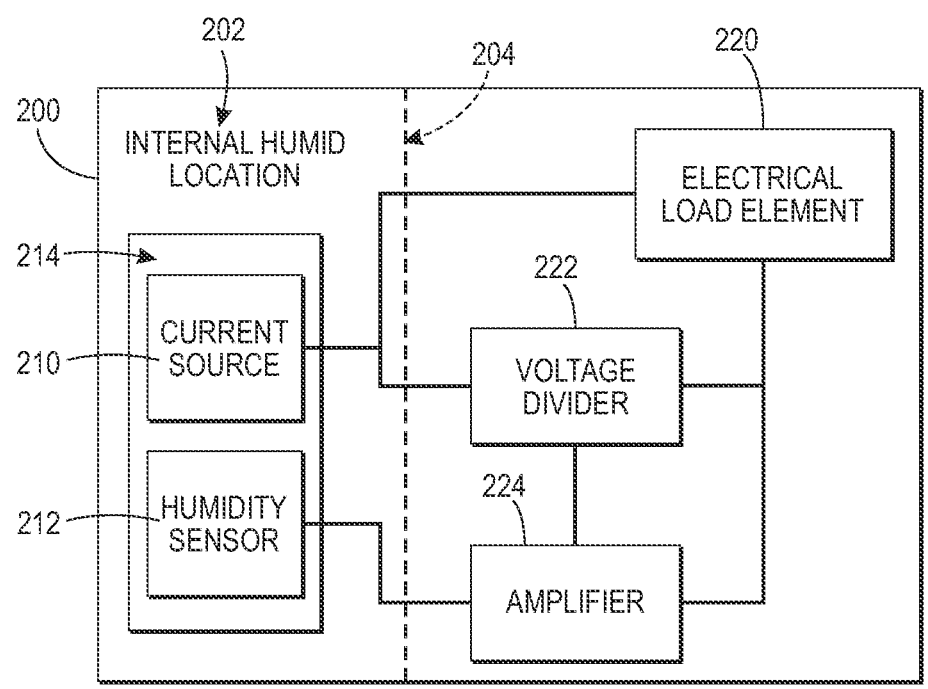
FIG. 3 is a schematic diagram illustrating devices herein.

As shown in FIG. 3, exemplary apparatuses (one of which is shown as item 200) herein have at least one internal humid location 202 (e.g., an internal location 202 that experiences a humidity level that is higher relative to the humidity levels of areas external to the apparatus 200). The area of relative higher humidity 202 can be less than the entire interior of the apparatus 200 (as represented by line 204) or the entire interior of the apparatus 200 can experience relative higher humidity.

The apparatus 200 utilizes at least one electrical current source 210 within the internal humid location 202 of the apparatus 200. Also, an electrical load element 220 is connected to the current source 210. The current source 210 provides primary output current (e.g., direct current (DC)) to the electrical load element 220. The current source 210 can experience undesirable leakage current that increases with increases in the humidity level of the humid location 202, and such increases in the leakage current caused by the increased humidity correspondingly decrease the primary output current provided to the electrical load element 220.

In order to address such issues, the apparatuses 200 herein include a voltage divider 222 that is connected to the current source 210, a humidity sensor 212 within the internal humid location 202 of the apparatus 200, and an amplifier 224 connected to the voltage divider 222 and the humidity sensor 212. The humidity sensor 212 produces a current signal that increases with increases in the humidity level and the amplifier 224 amplifies the signal produced by the humidity sensor 212 to produce compensating output current. The amplifier 224 provides amplification of the signal produced by the humidity sensor 212 at a level that increases with increases of the primary output current (as shown in FIG. 3, the primary output current is provided to the amplifier 224 by the voltage divider 222). Thus, the amplifier 224 provides the amplification of the signal produced by the humidity sensor 212 at a level to make the compensating output current equal to the leakage current.

Further, the amplifier 224 provides the compensating output current to the electrical load element 220 with the primary output current. This causes the electrical load element 220 to receive the primary output current combined with the compensating output current as a power supply current that is unaffected by (not decreased by) the leakage current.

Further, the current source 210 and the humidity sensor 212 can be located on the same printed circuit board 214 and can have substantially similarly sized and spaced elements (e.g., substantially similarly sized conductors and insulators) that react substantially similarly to the contamination and humidity that is found within the humid location 202 of the apparatus 200. Again, the contamination and humidity is responsible for causing much of the leakage current. Having substantially similarly sized conductors and insulators in the current source 210 and the humidity sensor 212 allows the amplified signal from the humidity sensor 212 to match the leakage current experienced by the current source 210, and thereby serves as a highly effective compensating output current supplementing the primary output current to allow the electrical load element 220 to receive a power supply current that is unaffected by the leakage current.

Figure 4:
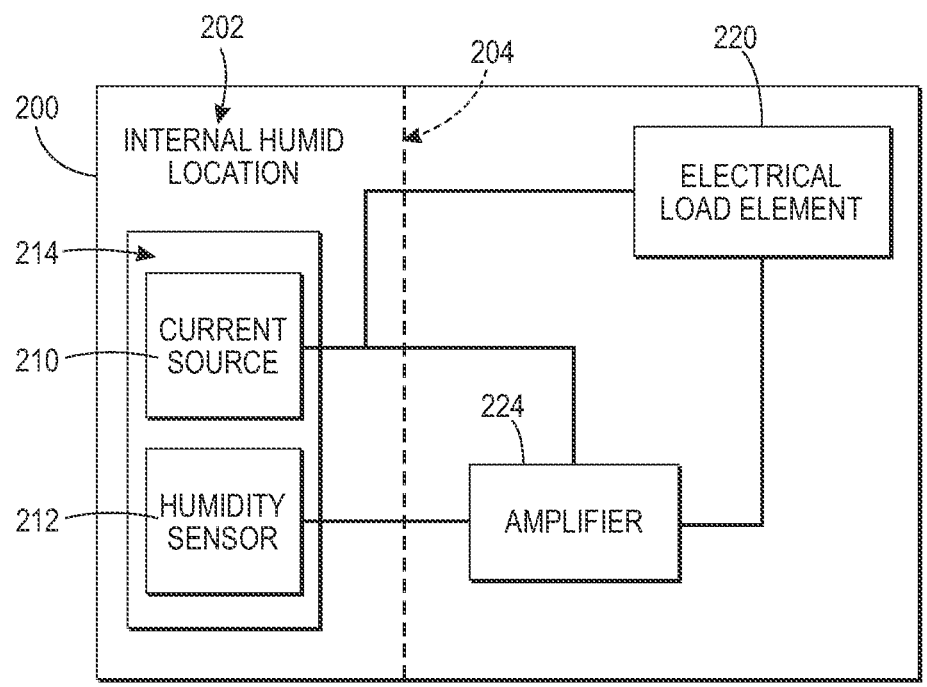
FIG. 4 is a schematic diagram illustrating devices herein.
Figure 5:
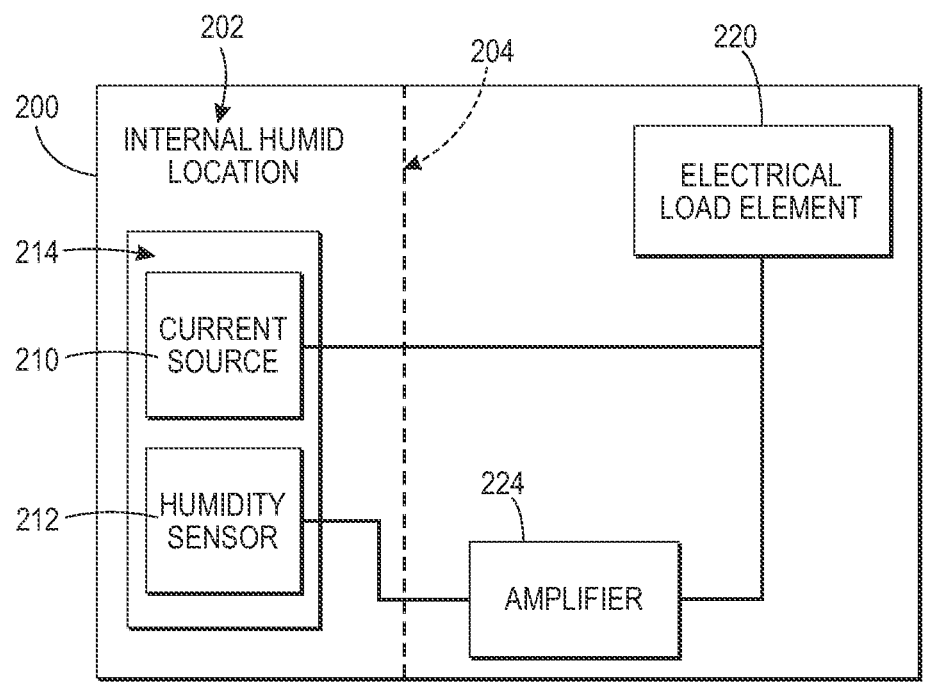
FIG. 5 is a schematic diagram illustrating devices herein.

In one example, the humidity sensor 212 can include opposing terminals, interleaved conductors connected to the terminals, and electrical insulation between the interleaved conductors (such as the interleaved conductors shown in item 120 in FIG. 2); however, those ordinarily skilled in the art would understand that any humidity sensor (or device/circuit that has conductivity affected by humidity and contamination) could be used as element 212. FIGS. 4 and 5 illustrate the same structure shown in FIG. 3; however, the structure shown in FIGS. 4 and 5 do without the voltage divider 222. The structure in FIG. 4 still supplies the output current to the amplifier 224 to allow the amplifier 224 to provide an increase in compensating output current as the primary output current increases. While the structure in FIG. 5 will not provide an increase in compensating output current as the primary output current increases, the structure in FIG. 5 still helps compensate for current leakage. Further, the structure shown in FIG. 5 provides a less expensive, smaller structure that is sufficient for certain situations. The structure of FIG. 4 also allows the amplifier to compensate for primary output current increases. Therefore, the structure of FIG. 4 does not have the reduced performance and is not a less expensive, smaller structure (although the block diagram may give that impression).

Figure 6:
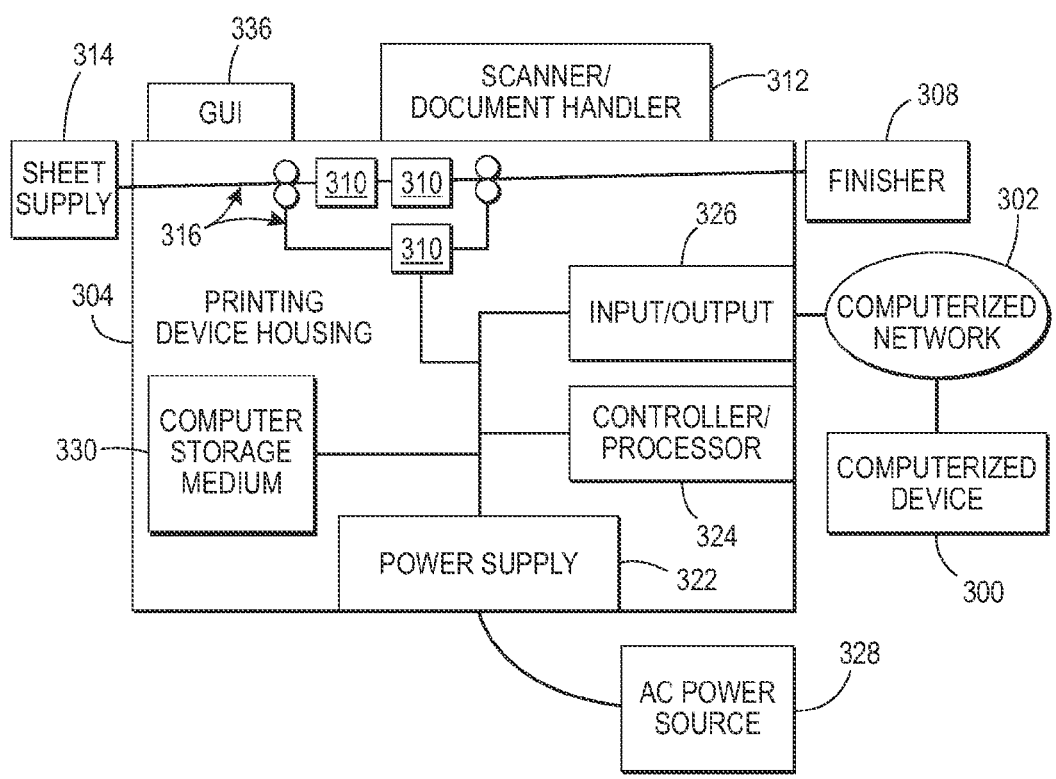
FIG. 6 is a schematic diagram illustrating devices herein.

FIG. 6 illustrates a computerized device that is a printing device 304, which can be used with systems and methods herein and can comprise, for example, a printer, copier, multi-function machine, multi-function device (MFD), etc. The printing device 304 includes a controller/processor 324 and a communications port (input/output) 326 operatively connected to the processor 324 and to the computerized network 302 external to the computerized device 300. Also, the printing device 304 can include at least one accessory functional component, such as a graphic user interface assembly 336 that also operate on the power supplied from the external power source 328 (through the power supply 322).

The input/output device 326 is used for communications to and from the computerized device 300. The processor 324 controls the various actions of the computerized device. A non-transitory computer storage medium device 330 (which can be optical, magnetic, capacitor based, etc.) is readable by the processor 324 and stores instructions that the processor 324 executes to allow the computerized device to perform its various functions, such as those described herein. Thus, as shown in FIG. 6, a body housing has one or more functional components that operate on power supplied from an alternating current (AC) source 328 by the power supply 322. The power supply 322 can comprise a power storage element (e.g., a battery, etc).

The printing device 304 includes at least one marking device (printing engines) 310 each of which includes the structures illustrated and discussed above (shown in FIGS. 2-5) that are operatively connected to the processor 324, a media path 316 positioned to supply sheets of media from a sheet supply 314 to the marking device(s) 310, etc. After receiving various markings from the printing engine(s), the sheets of media can optionally pass to a finisher 308 which can fold, staple, sort, etc., the various printed sheets. Also, the printing device 304 can include at least one accessory functional component (such as a scanner/document handler 312, etc.) that also operates on the power supplied from the external power source 328 (through the power supply 322).

All the schematic elements shown in FIGS. 3-6 are intended to represent all well-known similar devices that perform the same functions at those described above, whether currently known or developed in the future. Thus, the claims below are not limited by any illustration herein, because the illustrations are only examples to aid in the understanding of the structures herein.

Many computerized devices are discussed above. Computerized devices that include chip-based central processing units (CPU's), input/output devices (including graphic user interfaces (GUI), memories, comparators, processors, etc. are well-known and readily available devices produced by manufacturers such as Dell Computers, Round Rock Tex., USA and Apple Computer Co., Cupertino Calif., USA. Such computerized devices commonly include input/output devices, power supplies, processors, electronic storage memories, wiring, etc., the details of which are omitted herefrom to allow the reader to focus on the salient aspects of the systems and methods described herein. Similarly, scanners and other similar peripheral equipment are available from Xerox Corporation, Norwalk, Conn., USA and the details of such devices are not discussed herein for purposes of brevity and reader focus.

The terms printer or printing device as used herein encompasses any apparatus, such as a digital copier, bookmaking machine, facsimile machine, multi-function machine, etc., which performs a print outputting function for any purpose. The details of printers, printing engines, etc., are well-known and are not described in detail herein to keep this disclosure focused on the salient features presented. The systems and methods herein can encompass systems and methods that print in color, monochrome, or handle color or monochrome image data. All foregoing systems and methods are specifically applicable to electrostatographic and/or xerographic machines and/or processes.

In addition, terms such as "touching", "on", "in direct contact", "abutting", "directly adjacent to", etc., mean that at least one element physically contacts another element (without other elements separating the described elements). Further, the terms automated or automatically mean that once a process is started (by a machine or a user), one or more machines perform the process without further input from any user.

It will be appreciated that the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. Unless specifically defined in a specific claim itself, steps or components of the systems and methods herein cannot be implied or imported from any above example as limitations to any particular order, number, position, size, shape, angle, color, or material.

What is claimed is:

1. An apparatus comprising:
    an internal humid location having a humidity level that is higher relative to humidity levels of areas external to said apparatus;
    a current source within said internal humid location of said apparatus, said current source experiencing leakage current that increases with increases in said humidity level;
    a humidity sensor within said internal humid location of said apparatus, said humidity sensor producing a signal that increases with increases in said humidity level;
    an amplifier connected to said current source and said humidity sensor; and
    an electrical load element connected to said current source and said amplifier,
    said current source providing primary output current to said electrical load element,
    increases in said leakage current correspondingly decrease said primary output current,
    said amplifier amplifying said signal produced by said humidity sensor to produce compensating output current,
    said amplifier providing amplification of said signal produced by said humidity sensor at a level to make said compensating output current equal to said leakage current, and
    said amplifier providing said compensating output current to said electrical load element with said primary output current.

2. The apparatus according to claim 1, further comprising a printed circuit board within said internal humid location, said current source and said humidity sensor being located on said printed circuit board.

3. The apparatus according to claim 1, said compensating output current being provided with said primary output current causing said electrical load element to receive said primary output current combined with said compensating output current as a power supply current unaffected by said leakage current.

4. The apparatus according to claim 1, said humidity sensor comprising:
    opposing terminals;
    interleaved conductors connected to said terminals; and
    electrical insulation between said interleaved conductors.

5. The apparatus according to claim 1, said current source and said humidity sensor having substantially similarly sized and spaced elements that react substantially similarly to contamination and humidity.

6. The apparatus according to claim 1, said current source and said humidity sensor having substantially similarly sized and spaced conductors and insulators that react substantially similarly to contamination and humidity.

7. The apparatus according to claim 1, said current source experiencing leakage current that increases with increases in said primary output current.

8. An apparatus comprising:
an internal humid location having a humidity level that is higher relative to humidity levels of areas external to said apparatus;
a current source within said internal humid location of said apparatus, said current source experiencing leakage current that increases with increases in said humidity level;
a voltage divider connected to said current source;
a humidity sensor within said internal humid location of said apparatus, said humidity sensor producing a signal that increases with increases in said humidity level;
an amplifier connected to said voltage divider and said humidity sensor; and
an electrical load element connected to said current source and said amplifier,
said current source providing primary output current to said electrical load element,
increases in said leakage current correspondingly decrease said primary output current,
said amplifier amplifying said signal produced by said humidity sensor to produce compensating output current,
said amplifier providing amplification of said signal produced by said humidity sensor at a level that increases with increases of said primary output current as provided to said amplifier by said voltage divider,
said amplifier providing said amplification of said signal produced by said humidity sensor at said level to make said compensating output current equal to said leakage current, and
said amplifier providing said compensating output current to said electrical load element with said primary output current.

9. The apparatus according to claim 8, further comprising a printed circuit board within said internal humid location, said current source and said humidity sensor being located on said printed circuit board.

10. The apparatus according to claim 8, said compensating output current being provided with said primary output current causing said electrical load element to receive said primary output current combined with said compensating output current as a power supply current unaffected by said leakage current.

11. The apparatus according to claim 8, said humidity sensor comprising:
opposing terminals;
interleaved conductors connected to said terminals; and
electrical insulation between said interleaved conductors.

12. The apparatus according to claim 8, said current source and said humidity sensor having substantially similarly sized and spaced elements that react substantially similarly to contamination and humidity.

13. The apparatus according to claim 8, said current source and said humidity sensor having substantially similarly sized and spaced conductors and insulators that react substantially similarly to contamination and humidity.

14. The apparatus according to claim 8, said current source experiencing leakage current that increases with increases in said primary output current.

15. A printing apparatus comprising:
a printing engine;
an internal humid location in said printing engine having a humidity level that is higher relative to humidity levels of areas external to said printing engine;
a current source within said internal humid location of said printing apparatus, said current source experiencing leakage current that increases with increases in said humidity level;
a voltage divider connected to said current source;
a humidity sensor within said internal humid location of said printing apparatus, said humidity sensor producing a signal that increases with increases in said humidity level;
an amplifier connected to said voltage divider and said humidity sensor; and
an electrical load element connected to said current source and said amplifier,
said current source providing primary output current to said electrical load element,
increases in said leakage current correspondingly decrease said primary output current,
said amplifier amplifying said signal produced by said humidity sensor to produce compensating output current,
said amplifier providing amplification of said signal produced by said humidity sensor at a level that increases with increases of said primary output current as provided to said amplifier by said voltage divider,
said amplifier providing said amplification of said signal produced by said humidity sensor at said level to make said compensating output current equal to said leakage current, and
said amplifier providing said compensating output current to said electrical load element with said primary output current.

16. The printing apparatus according to claim 15, further comprising a printed circuit board within said internal humid location, said current source and said humidity sensor being located on said printed circuit board.

17. The printing apparatus according to claim 15, said compensating output current being provided with said primary output current causing said electrical load element to receive said primary output current combined with said compensating output current as a power supply current unaffected by said leakage current.

18. The printing apparatus according to claim 15, said humidity sensor comprising:
opposing terminals;
interleaved conductors connected to said terminals; and
electrical insulation between said interleaved conductors.

19. The printing apparatus according to claim 15, said current source and said humidity sensor having substantially similarly sized and spaced elements that react substantially similarly to contamination and humidity.

20. The printing apparatus according to claim 15, said current source and said humidity sensor having substantially similarly sized and spaced conductors and insulators that react substantially similarly to contamination and humidity.

* * * * *